US008742105B2

(12) United States Patent
Reddy et al.

(10) Patent No.: US 8,742,105 B2
(45) Date of Patent: Jun. 3, 2014

(54) POLYMORPHS OF RALTEGRAVIR POTASSIUM

(75) Inventors: Bandi Parthasaradhi Reddy, Andhra Pradesh (IN); Kura Rathnakar Reddy, Andhra Pradesh (IN); Rapolu Raji Reddy, Andhra Pradesh (IN); Dasari Muralidhara Reddy, Andhra Pradesh (IN); Kesireddy Subash Chander Reddy, Andhra Pradesh (IN)

(73) Assignee: Hetero Research Foundation (IN)

( * ) Notice: Subject to any disclaimer, the term of this patent is extended or adjusted under 35 U.S.C. 154(b) by 121 days.

(21) Appl. No.: 13/375,575

(22) PCT Filed: Jun. 2, 2009

(86) PCT No.: PCT/IN2009/000317
§ 371 (c)(1),
(2), (4) Date: Mar. 27, 2012

(87) PCT Pub. No.: WO2010/140156
PCT Pub. Date: Dec. 9, 2010

(65) Prior Publication Data
US 2012/0178930 A1    Jul. 12, 2012

(51) Int. Cl.
*C07D 413/12* (2006.01)

(52) U.S. Cl.
CPC ............ *C07D 413/12* (2013.01); *C07B 2200/13* (2013.01)
USPC ........................................................ 544/319

(58) Field of Classification Search
CPC .................................................. C07D 413/12

USPC ......................................................... 544/319
See application file for complete search history.

(56) References Cited

U.S. PATENT DOCUMENTS 7,754,731 B2    7/2010    Belyk et al.

FOREIGN PATENT DOCUMENTS

| WO | 03035077 A1 | 5/2003 |
| WO | 2006060681 A2 | 6/2006 |
| WO | 2006060712 A2 | 6/2006 |
| WO | 2011024192 A2 | 3/2011 |

OTHER PUBLICATIONS

Hancock, Pharm. Res 17 (4) 397 (2000).*
Vincenzo et al., "Discovery of Raltegravir, a Potent, Selective Orally Bioavailable HIV-Integrase Inhibitor for the Treatment of HIV-AIDS Invention", J. Med. Chem, 51, pp. 5843-5855, 2008.
International Search Report; International Application No. PCT/IN2009/000317; International Filing Date Jun. 2, 2009; 3 pages.
International Preliminary Report on Patentability and Written Opinion; International Application No. PCT/IN2009/000317; International Filing Date Jun. 2, 2009; 6 pages.

* cited by examiner

*Primary Examiner* — Noble Jarrell
*Assistant Examiner* — Valerie Rodriguez-Garcia
(74) *Attorney, Agent, or Firm* — Cantor Colburn LLP

(57) ABSTRACT

The present invention provides novel polymorphs of raltegravir potassium, processes for their preparation and pharmaceutical compositions comprising them. Thus for example, raltegravir potassium was added to water and stirred for 15 minutes, the solution was filtered on hiflo bed and the bed washed with water, the resulting solution was subjected to freeze drying at −180 deg C. for 13 hours to give raltegravir potassium amorphous form.

9 Claims, 4 Drawing Sheets

POLYMORPHS OF RALTEGRAVIR POTASSIUM

FIELD OF THE INVENTION

The present invention provides novel polymorphs of raltegravir potassium, processes for their preparation and pharmaceutical compositions comprising them.

BACKGROUND OF THE INVENTION

Inhibitors of human immunodeficiency virus (HIV) protease have been approved for use in the treatment of HIV infection for several years. A particularly effective HIV integrase inhibitor is N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide, also known as raltegravir and its pharmaceutically acceptable salts such as raltegravir potassium. Raltegravir is represented by the following structure.

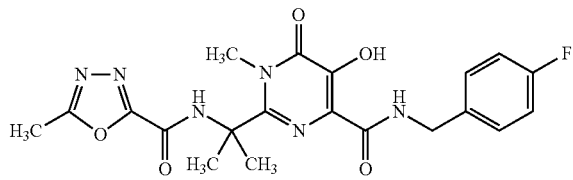 [SMILES: Cc1nnc(C(=O)NC(C)(C)c2nc(C(=O)NCc3ccc(F)cc3)c(O)c(=O)n2C)o1]

Polymorphism is defined as "the ability of a substance to exist as two or more crystalline phases that have different arrangement and/or conformations of the molecules in the crystal Lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Solvent medium and mode of crystallization play very important role in obtaining a crystalline form over the other.

Raltegravir can exist in different polymorphic forms, which differ from each other in terms of stability, physical properties, spectral data and methods of preparation.

WO Patent Publication No. 03/035077 disclosed N-substituted 5-hydroxy-6-oxo-1,6-dihydropyrimidine-4-carboxamides and pharmaceutically acceptable salts thereof. Processes for the preparations of raltegravir and related compounds were disclosed in WO Patent No. 03/035077. According to WO Patent No. 03/035077, raltegravir is prepared by reacting 5-methyl-1,3,4-oxadiazole-2-carboxylic acid with 2-(1-amino -1-methylethyl)-N-(4-fluorobenzyl)-5-hydroxy-1-methyl-6-oxo-1,6-dihydropyrimidine-4-carboxamide in acetonitrile in presence of triethyl amine and N,N-dimethylformamide.

WO Patent Publication No. 2006/060712 disclosed two crystalline forms of raltegravir potassium and processes for their preparation. The Publication described the formation of two crystalline forms of raltegravir potassium, which were designated raltegravir potassium salt of crystalline anhydrous Form 1 and hydrated Form 2.

According to the '712 patent publication, crystalline anhydrous form 1 of raltegravir potassium salt (characterized by an X-ray powder diffraction pattern having peaks expressed as 2θ at about 5.9, 12.5, 20.0, 20.6 and 25.6 degrees and further characterized by an differential scanning calorimetry exhibiting a single endotherm with a peak temperature of about 279 deg C.) can be prepared by crystallization of raltegravir potassium from mixing an aqueous solution of a potassium base with a mixture comprising raltegravir, water and alcohol to form a basic solution of raltegravir and filtering the solution. The resulting solution was seeded to provide the crystalline potassium salt of raltegravir.

According to the '712 patent publication, crystalline hydrated form 2 of raltegravir potassium salt (characterized by an X-ray powder diffraction pattern having peaks expressed as 2θ at about 7.9, 13.8, 15.7, 24.5 and 31.5 degrees and further characterized by an differential scanning calorimetry exhibiting two broad endotherms with peak temperatures of about 146 deg C. and 239 deg C. and a third sharp endotherm with a peak temperature of about 276 deg C.) can be prepared by crystallization of raltegravir potassium from solid potassium hydroxide and raltegravir were added to acetone, and the resulting solution was sonicated for several minutes until a precipitate formed. Then the resulting suction was filtered to dryness.

We have discovered that raltegravir can be prepared in well-defined and consistently reproducible amorphous form and crystalline form.

One object of the present invention is to provide a process for the preparation of amorphous form of raltegravir potassium and pharmaceutical compositions comprising it.

Another object of the present invention is to provide a novel crystalline form of raltegravir potassium and a process for preparing it and pharmaceutical compositions comprising it.

SUMMARY OF THE INVENTION

In accordance with one aspect of the present invention, there is provided a process for preparation of raltegravir potassium amorphous form, which comprises freeze drying an aqueous solution of raltegravir potassium at −170 to −180 deg C. to obtain raltegravir potassium amorphous form.

In accordance with another aspect of the present invention, there is provided a process for the preparation of raltegravir potassium amorphous form, which comprises:

a) stirring raltegravir potassium in water;
b) removing the water from the solution obtained in step (a) to obtain a solid;
c) slurrying the solid obtained in step (b) with an organic solvent; and
d) isolating raltegravir potassium amorphous form.

In accordance with another aspect of the present invention, there is provided a novel crystalline form of raltegravir potassium designated as form H1 characterized by peaks in the powder x-ray diffraction spectrum having 2θ angle positions at about 5.2, 6.9, 9.0, 13.9, 21.5 and 23.0±0.2 degrees.

In accordance with another aspect of the present invention, there is provided a process for the preparation of raltegravir potassium crystalline form H1, which comprises:

a) providing a solution of raltegravir potassium in dimethylformamide or dimethylacetamide or mixture thereof, optionally mixed with one or more other solvent;
b) separating solid from the solution obtained in step (a); and
c) isolating raltegravir potassium crystalline form H1.

In accordance with another aspect of the present invention, there is provided a pharmaceutical composition comprising a polymorphic form of raltegravir potassium selected from form H1 and amorphous form or a mixture thereof; and a pharmaceutically acceptable excipient.

DETAILED DESCRIPTION OF THE INVENTION

The powdered x-ray diffractogram (PXRD) of raltegravir potassium amorphous form is shown in FIG. 1.

Raltegravir potassium amorphous form of present invention is further characterized by a Differential Scanning calorimetry (DSC) thermogram as shown in FIG. 2.

Freeze drying is the term used, freezing the material and then reducing the surrounding pressure and adding enough heat to allow the frozen water in the material to sublime directly from the solid phase to gas.

In accordance with one aspect of the present invention, there is provided a process for preparation of raltegravir potassium amorphous form, which comprises freeze drying an aqueous solution of raltegravir potassium at −170 to −180 deg C. to obtain raltegravir potassium amorphous form.

In accordance with another aspect of the present invention, there is provided a process for the preparation of raltegravir potassium amorphous form, which comprises:
a) stirring raltegravir potassium in water;
b) removing the water from the solution obtained in step (a) to obtain a solid;
c) slurrying the solid obtained in step (b) with an organic solvent; and
d) isolating raltegravir potassium amorphous form.

The organic solvent used in step (c) is a solvent or a mixture of solvents and may be selected from the group consisting of a heptane, hexane, diethyl ether, cyclohexane, n-hexanol, n-octanol, 3-ethyl-3-pentanol, polyethylene glycol, isopropyl acetate, n-butyl acetate, glycerol triacetate, acetone, methyl isobutyl ketone, 2,4-dimethylpentanone, alpha-tetralone, methyl t-butyl ether, 2,2,4,4-tetramethyltetrahydrofuran, toluene, tetralin, nitrobenzene, p-xylene, sulfolane and decalin. Preferable organic solvent is selected from heptane, hexane, diethyl ether and cyclohexane, still more preferable organic solvent is heptane.

Raltegravir potassium used in the process of the present invention may be in the form of hydrated and anhydrous. Thus, for example, raltegravir potassium anhydrous crystalline form 1 and raltegravir potassium hydrated crystalline form 2 may be used.

The water may be removed from the solution in step (b) by known methods, for example, distillation or spray drying.

The distillation of the solvent may be carried out at atmospheric pressure or at reduced pressure. The distillation may also preferably be carried out until the solvent is almost completely distilled off.

The temperature at which slurrying is carried out is not critical and the slurrying may conveniently be carried out at room temperature.

The isolation of raltegravir potassium amorphous form may be performed by conventional techniques such as centrifugation and filtration.

In accordance with another aspect of the present invention, there is provided a novel crystalline form of raltegravir potassium designated as form H1 characterized by peaks in the powder x-ray diffraction spectrum having 2θ angle positions at about 5.2, 6.9, 9.0, 13.9, 21.5 and 23.0±0.2 degrees. The powdered x-ray diffractogram (PXRD) of raltegravir potassium crystalline form H1 is shown in FIG. 3.

Raltegravir potassium crystalline form H1 of present invention is further characterized by a Differential Scanning calorimetry (DSC) thermogram as shown in FIG. 4.

The raltegravir potassium crystalline form H1 may be identified and differentiated from the known polymorphs by its characteristic PXRD pattern. Thus, for example, a peak at 5.2±0.2 degrees 2θ is present and a peak at 12.5±0.2 degrees 2θ is absent in the PXRD of the raltegravir potassium crystalline form H1 of the present invention, but the peak at 5.2±0.2 degrees 2θ is absent and a peak at 12.5±0.2 degrees 2θ is present in the PXRD of the raltegravir potassium anhydrous crystalline form 1 disclosed in the WO Patent Publication No. 2006/060712.

In accordance with another aspect of the present invention, there is provided a process for the preparation of raltegravir potassium crystalline form H1, which comprises:
a) providing a solution of raltegravir potassium in dimethylformamide or dimethylacetamide or mixture thereof, optionally mixed with one or more other solvent;
b) separating solid from the solution obtained in step (a); and
c) isolating raltegravir potassium crystalline form H1.

Raltegravir potassium used in the process of the present invention may be in the form of hydrated, anhydrous and amorphous. Thus, for example, raltegravir potassium amorphous form, raltegravir potassium anhydrous crystalline form 1 and raltegravir potassium hydrated crystalline form 2 may be used. Preferable raltegravir potassium amorphous form is used.

The other solvent used in step (a) is an inorganic solvent or an organic solvent and may be selected from the group consisting of a water, dimethyl sulfoxide, liquid ammonia, cyclohexane and hexane. Preferable other solvent is water.

The isolation of raltegravir potassium crystalline form H1 may be performed by conventional techniques such as centrifugation and filtration.

In accordance with another aspect of the present invention, there is provided a pharmaceutical composition comprising a polymorphic form of raltegravir potassium selected from form H1 and amorphous form or a mixture thereof; and a pharmaceutically acceptable excipient.

The pharmaceutical dosage form may preferably be in an oral dosage form.

Figure 1:
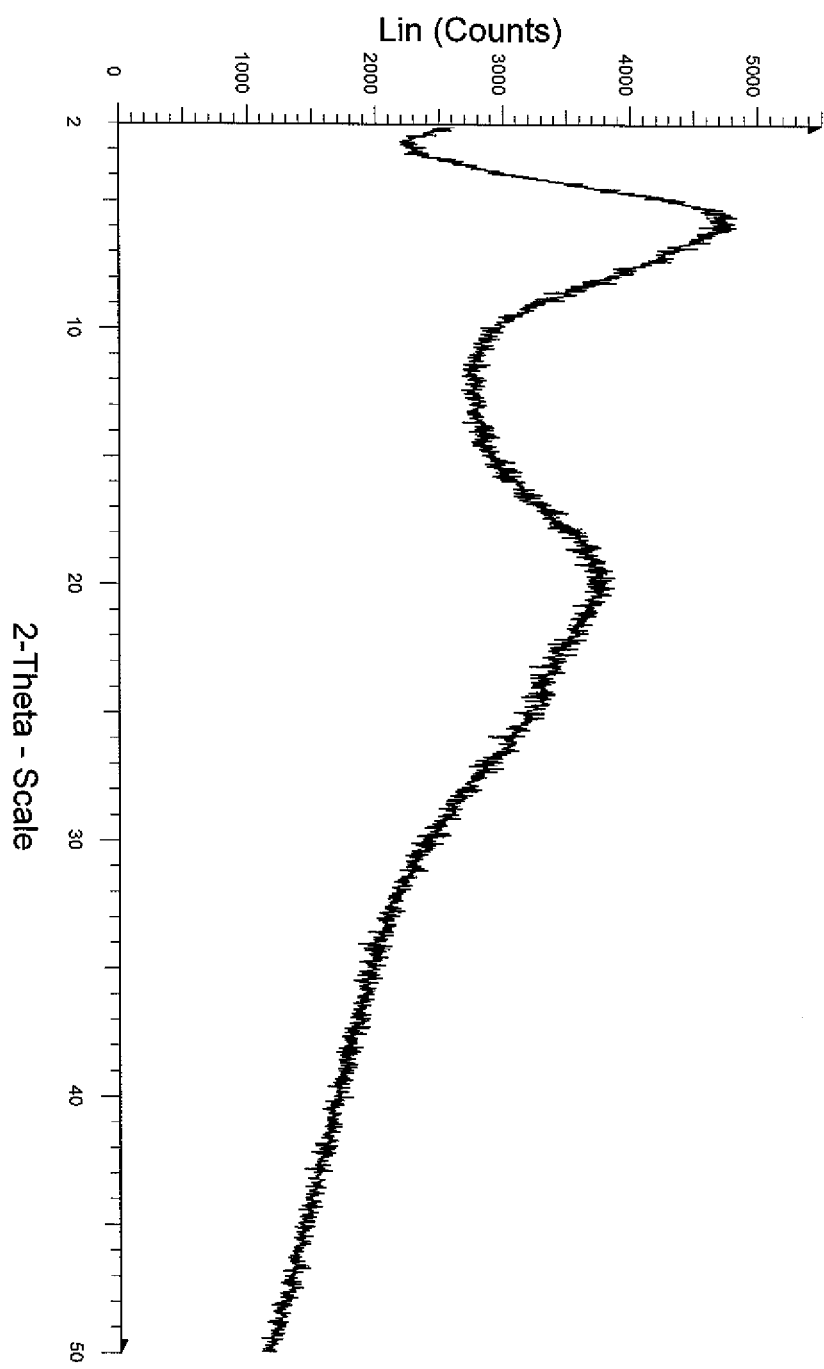
FIG. 1 is X-ray powder diffraction spectrum of raltegravir potassium amorphous form.
Figure 2:
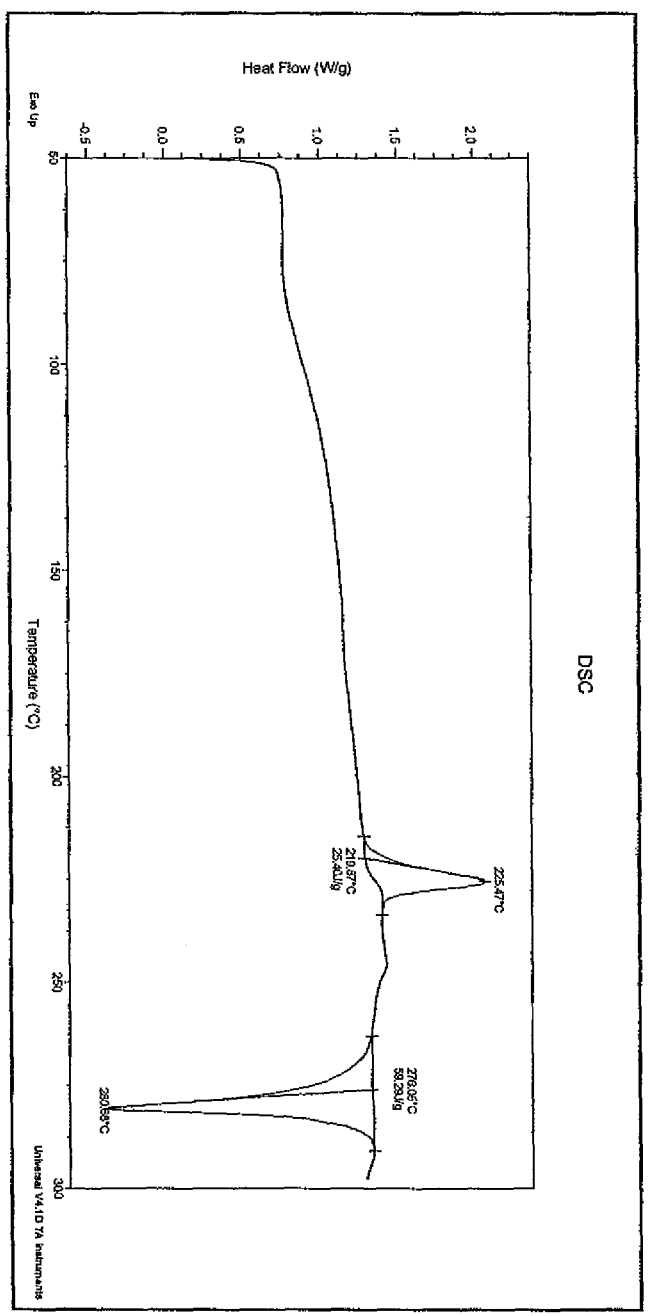
FIG. 2 is Differential scanning calorimetry (DSC) thermogram of raltegravir potassium amorphous form.
Figure 3:
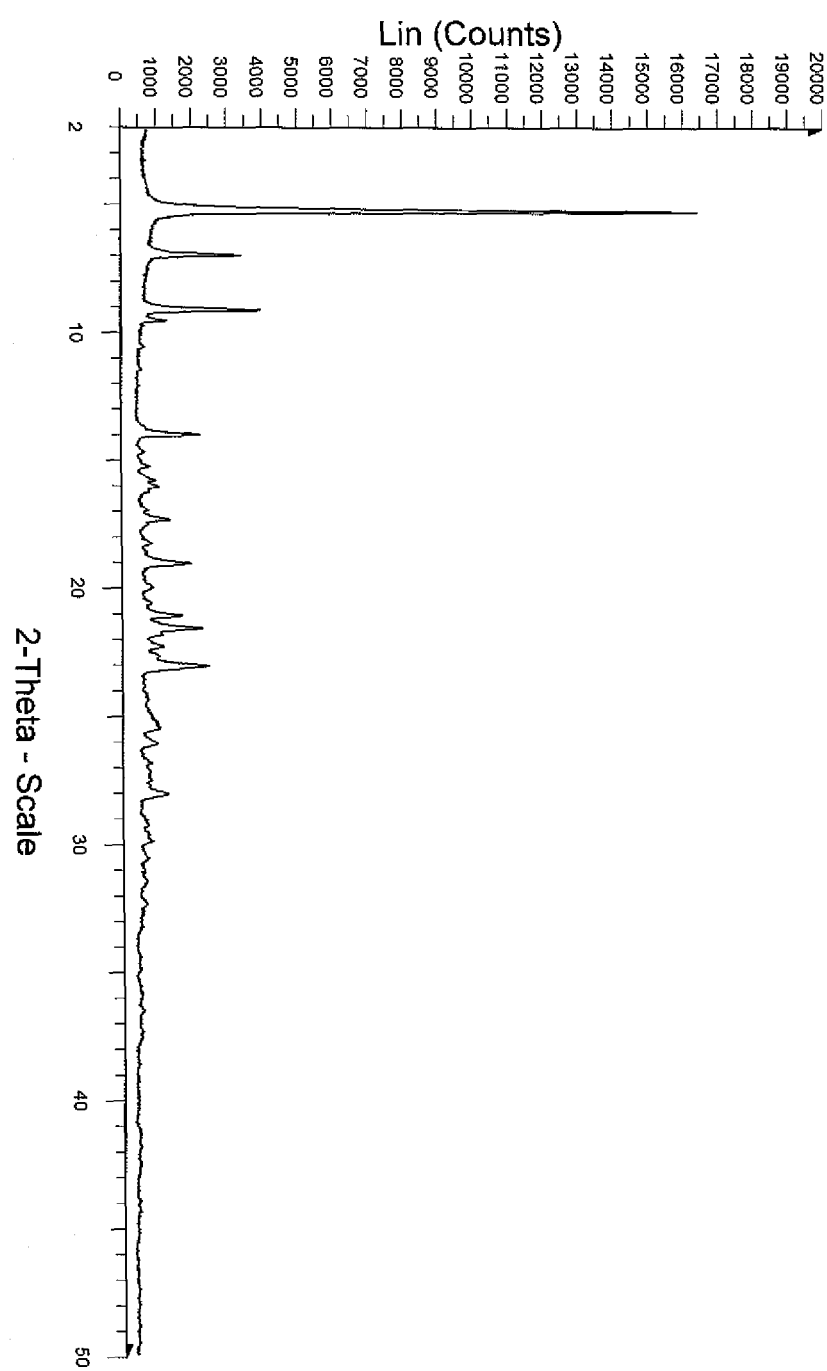
FIG. 3 is X-ray powder diffraction spectrum of raltegravir potassium crystalline form H1.
Figure 4:
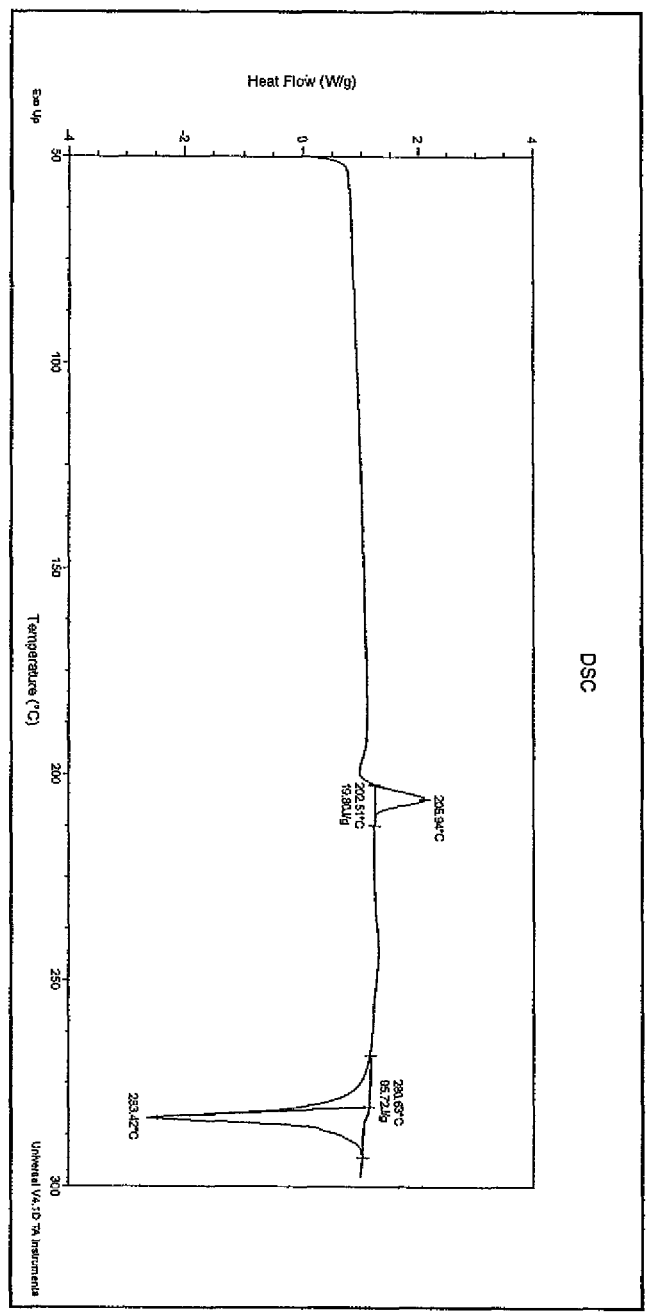
FIG. 4 is Differential scanning calorimetry (DSC) thermogram of raltegravir potassium crystalline form H1.

X-ray powder diffraction spectrum was measured on a bruker axs D8 advance X-ray powder diffractometer having a copper-Kα radiation. Approximately 1 gm of sample was gently flattered on a sample holder and scanned from 2 to 50 degrees two-theta, at 0.02 degrees to theta per step and a step of 52 seconds. The sample was simply placed on the sample holder. The sample was rotated at 30 rpm at a voltage 40 KV and current 35 mA.

DSC (Differential Scanning calorimetry) measurements were performed with a DSC Q10 (TA Instruments, Inc.). About 2.3 mg of the powder was placed in an open aluminum pan and it was crimped with an aluminum lid. The crimped sample was then placed in the DSC cell opposite to empty aluminum pan (as reference) and the sample was scanned at 10 deg C./min from 50 deg C. to 300 deg C.

The invention will now be further described by the following examples, which are illustrative rather than limiting.

EXAMPLES

Example 1

Raltegravir potassium (25 gm) was dissolved in water (350 ml), stirred for 15 minutes at room temperature. The solution was filtered on hiflo bed and the bed washed with water (25 ml). The resulting solution was subjected to freeze drying at −180 deg C. for 13 hours to obtain 25 gm of raltegravir potassium amorphous form.

Example 2

Raltegravir potassium anhydrous crystalline form 1 (10 gm) was dissolved in water (150 ml), stirred for 15 minutes at room temperature. The solution was filtered on hiflo bed, the bed washed with water and distilled off the water under vacuum at 55 to 60 deg C. to obtain solid. To the solid was added heptane (100 ml), distilled off the solvent and solid was collected. The solid was taken in heptane (100 ml), stirred for 2 hours at room temperature, filtered, washed the solid with heptane and dried the solid at 90 to 100 deg C. for 5 hours to obtain 9.5 gm of raltegravir potassium amorphous form.

Example 3

Raltegravir potassium amorphous form (10 gm) as obtained in example 2 was dissolved in dimethylformamide (100 ml) at room temperature. The solution was stirred for 1 hour at room temperature and separated the solid. The solid was stirred for 24 hours at room temperature, filtered, washed the solid with dimethylformamide and dried at 115 to 120 deg C. for 48 hours to obtain 10 gm of raltegravir potassium crystalline form H1.

Example 4

Raltegravir (10 gm) was dissolved in dimethylformamide (100 ml) at room temperature and cooled to 10 to 15 deg C. To the reaction mass was added slowly a mixture of potassium hydroxide (1.5 gm) and water (2 ml) at 10 to 15 deg C. and the temperature was raised to 25 to 30 deg C., filtered. The solid obtained was washed with dimethylformamide and dried at 110 to 120 deg C. for 48 hours to obtain 7 gm of raltegravir potassium crystalline form H1.

We claim:

1. A process for the preparation of raltegravir potassium amorphous form comprising
    a. stirring raltegravir potassium in water;
    b. removing the water from the solution obtained in step (a) to obtain a solid;
    c. slurrying the solid obtained in step (b) with an organic solvent; and
    d. isolating raltegravir potassium amorphous form from the slurry.

2. The process as claimed in claim 1, wherein the organic solvent used in step (c) is a solvent or a mixture of solvents and selected from the group consisting of heptane, hexane, diethyl ether, cyclohexane, n-hexanol, n-octanol, 3-ethyl-3-pentanol, polyethylene glycol, isopropyl acetate, n-butyl acetate, glycerol triacetate, acetone, methyl isobutyl ketone, 2,4-dimethylpentanone, alpha-tetralone, methyl t-butyl ether, 2,2,4,4-tetramethyltetrahydrofuran, toluene, tetralin, nitrobenzene, p-xylene, sulfolane and decalin.

3. The process as claimed in claim 2, wherein the organic solvent used in step (c) is selected from group consisting of heptane, hexane, diethyl ether and cyclohexane.

4. The process as claimed in claim 3, wherein the organic solvent used in step (c) is heptane.

5. The process as claimed in claim 1, wherein the raltegravir potassium used in step (a) is in the form of hydrated or anhydrous.

6. The process as claimed in claim 5, wherein the raltegravir potassium used in step (a) is in the form of raltegravir potassium anhydrous crystalline form 1 or raltegravir potassium hydrated crystalline form 2.

7. The process as claimed in claim 1, wherein the water in step (b) is removed by distillation or spray drying.

8. The process as claimed in claim 7, wherein distillation is carried out at atmospheric pressure or at a reduced pressure.

9. The process as claimed in claim 8, wherein distillation is carried out at 55 to 60° C. under vacuum.

* * * * *